(12) United States Patent
Yamamori et al.

(10) Patent No.: US 6,512,581 B1
(45) Date of Patent: Jan. 28, 2003

(54) RESPIRATORY GAS SENSOR

(75) Inventors: Shinji Yamamori, Tokyo (JP); Noriaki Todokoro, Tokyo (JP); Hidetoshi Dainobu, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 10 days.

(21) Appl. No.: 09/599,574

(22) Filed: Jun. 23, 2000

Related U.S. Application Data

(63) Continuation-in-part of application No. 09/334,564, filed on Jun. 21, 1999, now Pat. No. 6,216,692.

(30) Foreign Application Priority Data

| Jun. 19, 1998 | (JP) | 10-172455 |
| Jun. 23, 1999 | (JP) | 11-176709 |
| May 12, 2000 | (JP) | 2000-139679 |

(51) Int. Cl.$^7$ .............................. G01N 1/10; G01N 1/22
(52) U.S. Cl. .......................................... 356/246; 422/84
(58) Field of Search ................. 356/244, 246; 73/23.2, 23.3; 250/339.13; 422/84

(56) References Cited

U.S. PATENT DOCUMENTS

| 4,914,720 A | * | 4/1990 | Knodle et al. ............... 250/343 |
| 5,067,492 A | * | 11/1991 | Yelderman et al. ......... 128/719 |
| 5,789,660 A | * | 8/1998 | Kofoed et al. ............... 73/23.2 |
| 5,957,127 A | * | 9/1999 | Yamamori et al. ...... 128/204.22 |
| 6,216,692 B1 | | 4/2001 | Todokoro et al. ....... 128/205.23 |

FOREIGN PATENT DOCUMENTS

JP 4-48534 11/1992 ......... G01N/33/497

* cited by examiner

*Primary Examiner*—Michael P. Stafira
(74) *Attorney, Agent, or Firm*—Sughrue Mion, PLLC

(57) ABSTRACT

An airway adaptor 11 formed of a tubular member is narrowed in diameter at its central part in an axial direction to form parallel faces 11a, and the parallel faces 11a are formed with optical windows 12, 13 on a same axis. An adaptor 17 fitted in the airway adaptor 11 is formed with parallel faces at positions respectively facing with the optical windows 12, 13 leaving determined slits 17f therebetween and provided with a through hole 17c on a same axis as the optical windows 12, 13.

42 Claims, 11 Drawing Sheets

RESPIRATORY GAS SENSOR

This is a Continuation-In-Part Application of Ser. No. 09/334,564 filed on Jun. 21, 1999 now U.S. Pat. No. 6,216,692.

BACKGROUND OF INVENTION

1. Field of Invention

The present invention relates to a respiratory gas sensor which is used for measuring gas concentration in respiratory gas from a living body or determining whether the living body breathes or not, and more particularly to the respiratory gas sensor (hereinafter referred to simply as "a sensor") which is suitable in case where a target to be measured is a living body whose tidal volume is relatively small.

2. Related Art

As an apparatus for measuring the concentration of the gas such as carbon dioxide gas in the expiratory gas from the living body, there has been known such a sensor disclosed in Examined Japanese Utility Model Publication Hei. 4-48534. A structure of this sensor is shown in FIG. 14. FIG. 14 is a sectional view of an essential part showing a function of the sensor in an enlarged scale.

In the drawings, a sensor 1 includes an airway adaptor 2 which is a tubular member, a light source 3 and an infrared detecting portion 4 which are provided on an outer periphery of the airway adaptor 2 at an approximately right angle with respect to an axis of the airway adaptor 2. These light source 3 and infrared detecting portion 4 are provided on a same optical axis so that infrared light passes through the airway adaptor 2 in a direction of an approximately right angle with respect to its axis through optical windows 5, 6 which are airtightly provided in an outer wall of the airway adaptor 2. The infrared detecting portion 4 detects only light having a wavelength which has been absorbed by the gas in the respiratory gas flowing through the airway adaptor 2, such as carbon dioxide gas, and the gas concentration is measured by as known technique.

When the gas concentration is measured by the sensor 1 having the above described structure, in case where an inner volume of the respiratory gas sensor is large, the sensor 1 cannot be used for the living body which has a small tidal volume such as a neonatal and pediatric patient, because its dead space volume is too large. In order to solve this problem, there has been provided, in the publication described above, a tubular adaptor 7 which is fitted with an inner peripheral face of the airway adaptor 2 and formed with a through hole 7a at a position in alignment with the optical windows 5, 6 as shown in FIG. 14. With this structure, the inner volume of the sensor 1 is substantially reduced, and the dead space volume will be decreased. As a result, the concentration of the gas such as carbon dioxide gas in the respiratory gas from the neonatal and pediatric patient who has the small tidal volume can be efficiently measured.

However, in the conventional sensor constructed as above, the respiratory gas flows through a through hole 7b having a small inner diameter in a center part of the adaptor 7, and only a central portion of light which is irradiated from the light source 3 passes through the respiratory gas. For this reason, an amount of the light to be detected by the infrared detecting portion 4 is decreased, resulting in deterioration of measuring accuracy.

Further, the respiratory gas has generally humidity of almost 100%. Therefore, when measurements have been repeated several times, waterdrops caused by humidity gather to be a waterlayer 8, and the waterlayer may remain in the through holes 7a facing the optical windows 5, 6 provided in the adaptor 7 and will not flow out outside, as shown in FIG. 14. As a result, the waterlayer interrupts the light to cause a measurement error.

SUMMARY OF INVENTION

The invention has been made in view of the above circumstances, and an object of the present invention is to provide a respiratory gas sensor having a simple structure which can efficiently measure the gas concentration in the respiratory gas from the living body which has the small tidal volume, with high accuracy and without an influence caused by the waterdrops and the waterlayer.

In order to attain the above described object, according to an aspect of the present invention, a respiratory gas sensor includes a tubular member including a pathway formed therein, a pair of optical windows formed airtightly in a circumferential wall of the tubular member for allowing light to pass through said optical windows from the exterior into the gas flowing through the pathway, an adaptor fitted to an inner peripheral face of the tubular member and provided with a through hole at a position in alignment with the optical windows, and slits formed in the adaptor in an axis direction in such a manner that the slits face and position adjacent to the optical windows formed on the outer periphery of the tubular member, respectively, and each slit having a width larger than that of the optical window in a direction orthogonal to the axis direction of said pathway.

According to a second aspect of the present invention, as a respiratory gas sensor as mentioned in the first aspect of the present invention, the adaptor is divided in axially opposite sides of the optical windows.

According to a third aspect of the present invention, as a respiratory gas sensor as mentioned in the second aspect of the present invention, the adaptor to be divided is fixed inside the tubular member.

According to a fourth aspect of the present invention, as a respiratory gas sensor as mentioned in the second aspect of he present invention, the adaptor to be divided is detachably connected with each other inside the tubular member.

According to a fifth aspect of the present invention, as a respiratory gas sensor as mentioned in the first to fourth aspects of the present invention, anti-fogging films are provided on inner faces of the optical windows.

According to a sixth aspect of the present invention, there is provided a respiratory gas sensor including a tubular member including a pathway formed therein, and a pair of optical windows formed airtightly in a peripheral wall of the tubular member for allowing light to pass through said optical windows from the exterior into the gas flowing through the pathway, a partitioning portion for dividing the pathway into plurality of passages, the partitioning portion including a through hole for allowing light to pass through from one of the optical windows to the other, the passages divided by the partitioning portion being adapted to extend along the optical windows respectively and each having a width larger than that of each of the optical windows in a direction orthogonal to the pathway According to a seventh aspect of the present invention, as a respiratory gas sensor as mentioned in the sixth aspect of the present invention, anti-fogging films are provided on inner faces of the optical windows.

According to the present invention, the adaptor is formed with the slits on its outer periphery at positions respectively facing with and adjacent to the optical windows in an axial direction along the entire length of the adaptor, each of the slits having a width larger than that of each of the optical windows in a direction orthogonal to the axis direction of said pathway. Therefore, the whole light generated from the light source and passing through the optical windows can irradiate the respiratory gas which passes through the pathway and the concentration of the gas can be measured efficiently and with high accuracy. Further, as the slits are formed in adjacent to the optical windows, the waterdrops will not remain on the inner faces of the optical windows.

According to the second to fourth aspects of the present invention, the adaptor is divided so that a molding operation can be simply subjected. In this case, the adaptor to be divided may be fixed to the tubular member or detachably connected thereto. By constructing the adaptor to be detachable, the adaptor can be taken out from the tubular member after the use, then cleaned and sterilized to be reusable.

According to the fifth aspect of the present invention, the anti-fogging films are provided on the inner faces of the optical windows, thereby preventing the inner faces of the optical windows from fogging by humidity of the respiratory gas which passes through the slits.

According to the sixth aspect of the present invention, there is achieved to a similar function to the first aspect of the present invention.

According to the seventh aspect of the present invention, there is achieved to a similar function to the fifth aspect of the present invention.

DETAILED DESCRIPTION OF PREFERRED EMBODIMENTS

Figure 1:
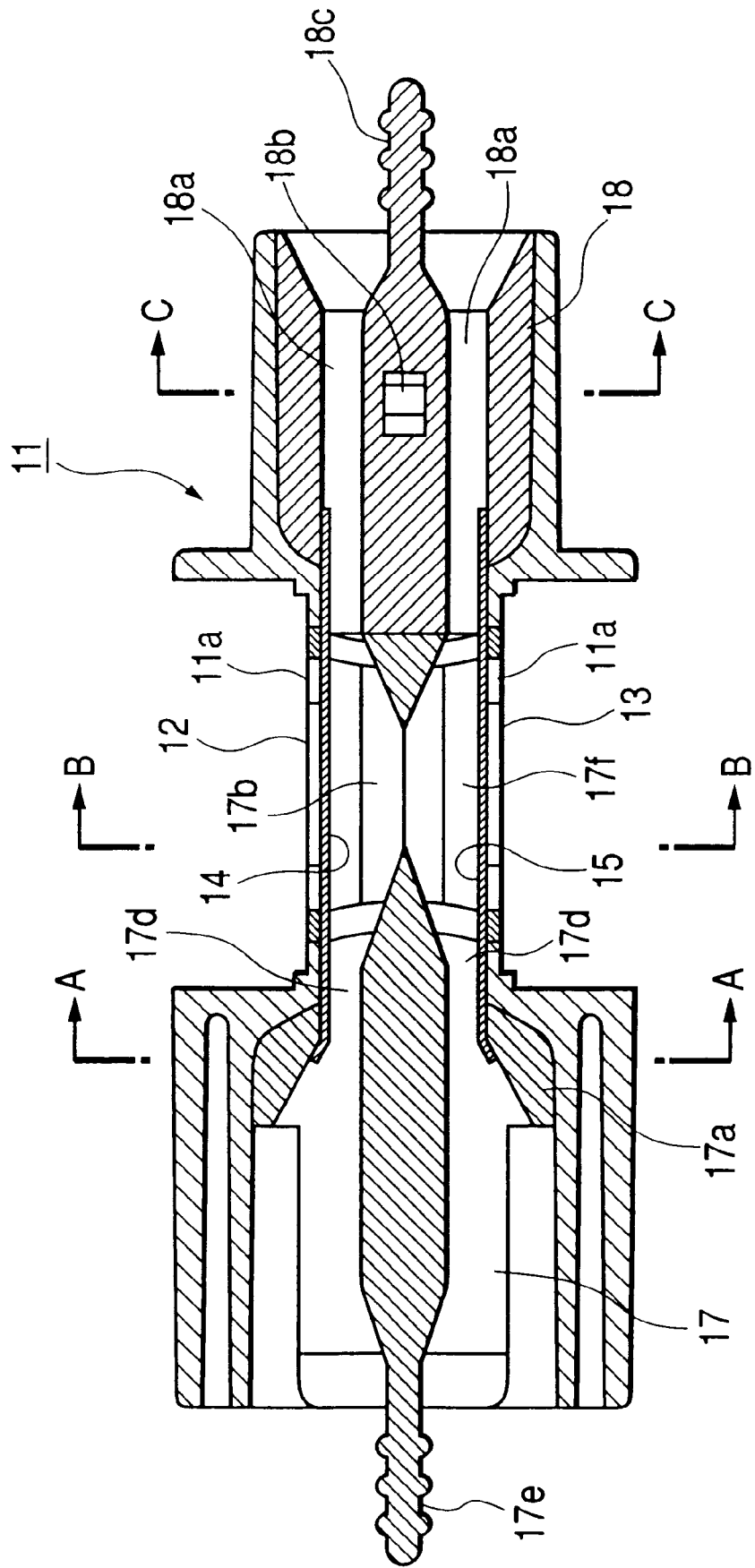
FIG. 1 is a longitudinally sectional view of a respiratory gas sensor according to an embodiment of the invention showing an airway adaptor provided with an adaptor.
Figure 2:
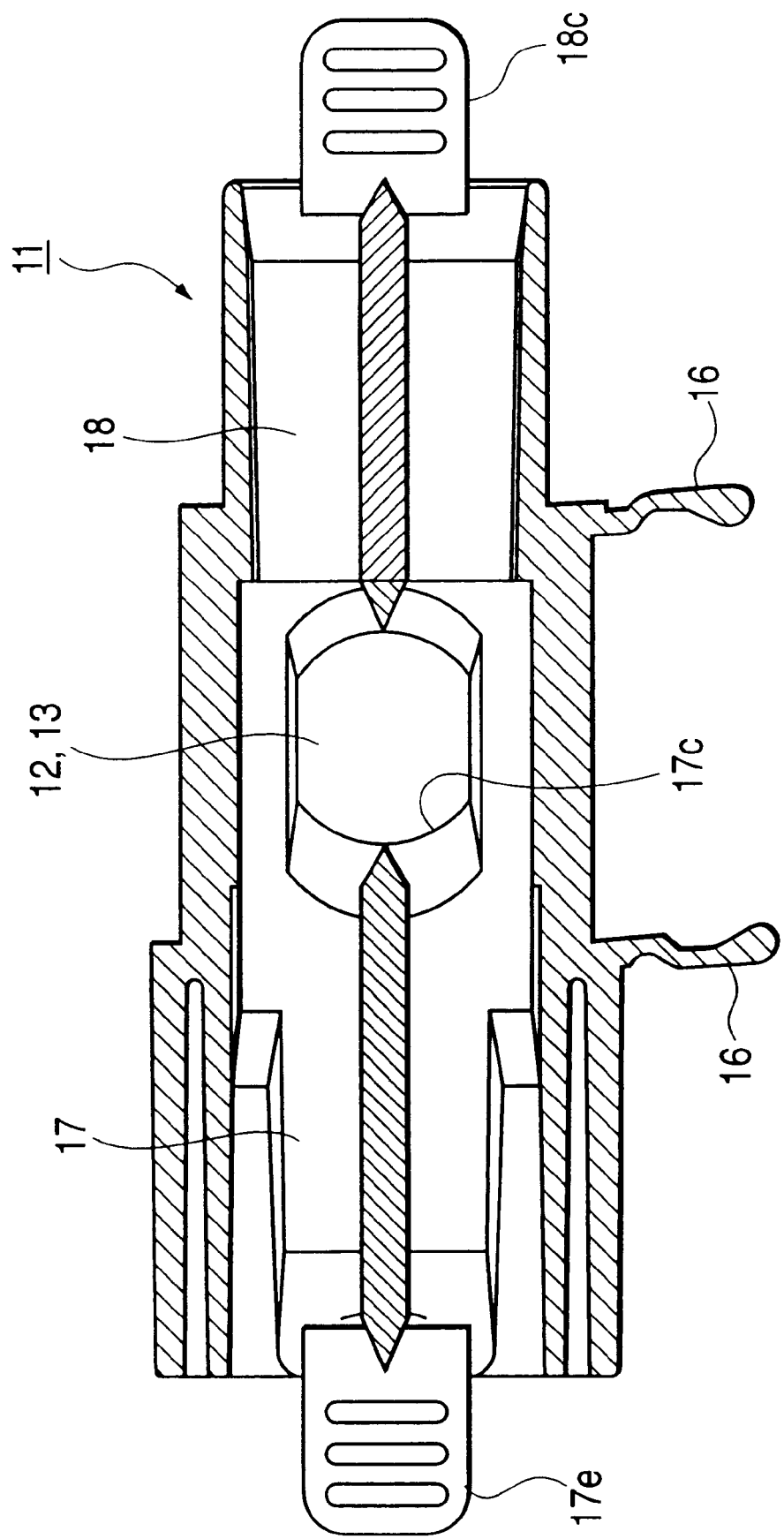
FIG. 2 is a sectional plan view of FIG. 1.
Figure 3:
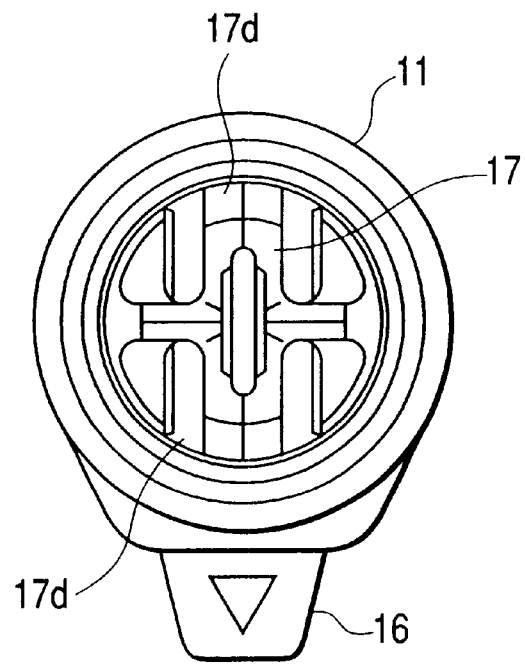
FIG. 3 is a left side view of FIG. 2.
Figure 4:
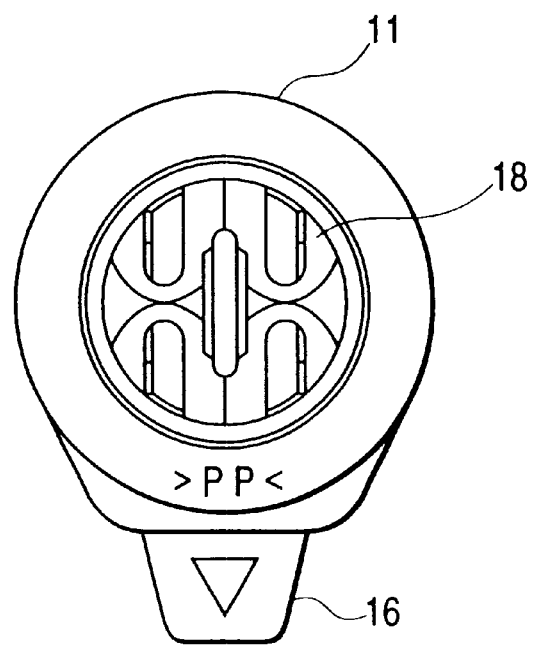
FIG. 4 is a right side view of FIG. 2.
Figure 5:
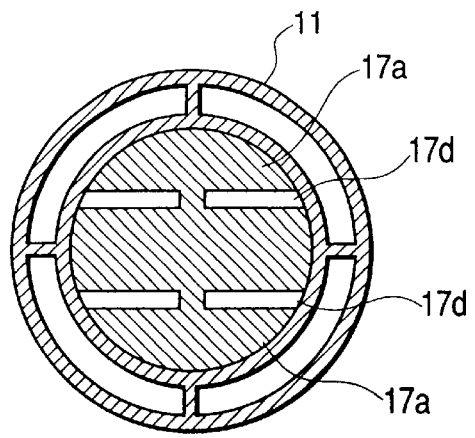
FIG. 5 is a sectional view taken along a line A—A in FIG. 1.
Figure 6:
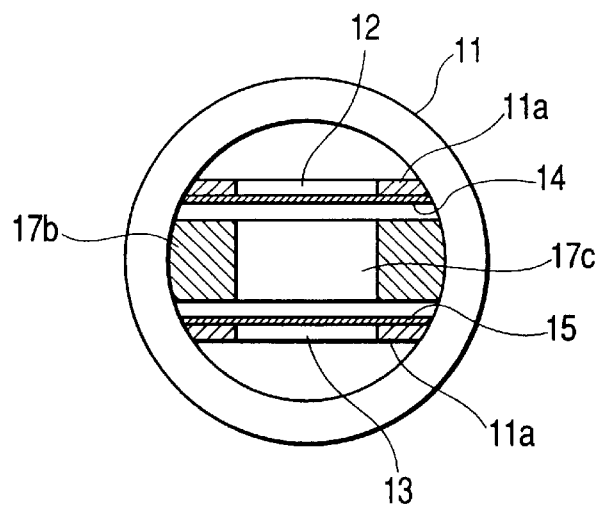
FIG. 6 is a sectional view taken along a line B—B in FIG. 1.
Figure 7:
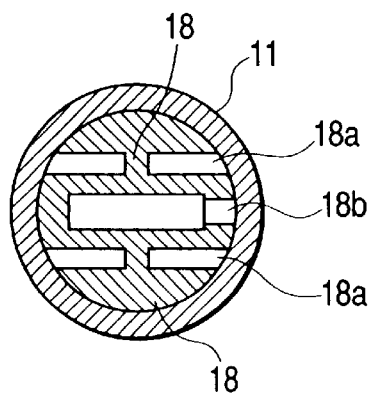
FIG. 7 is a sectional view taken along a line C—C in FIG. 1.
Figure 8:
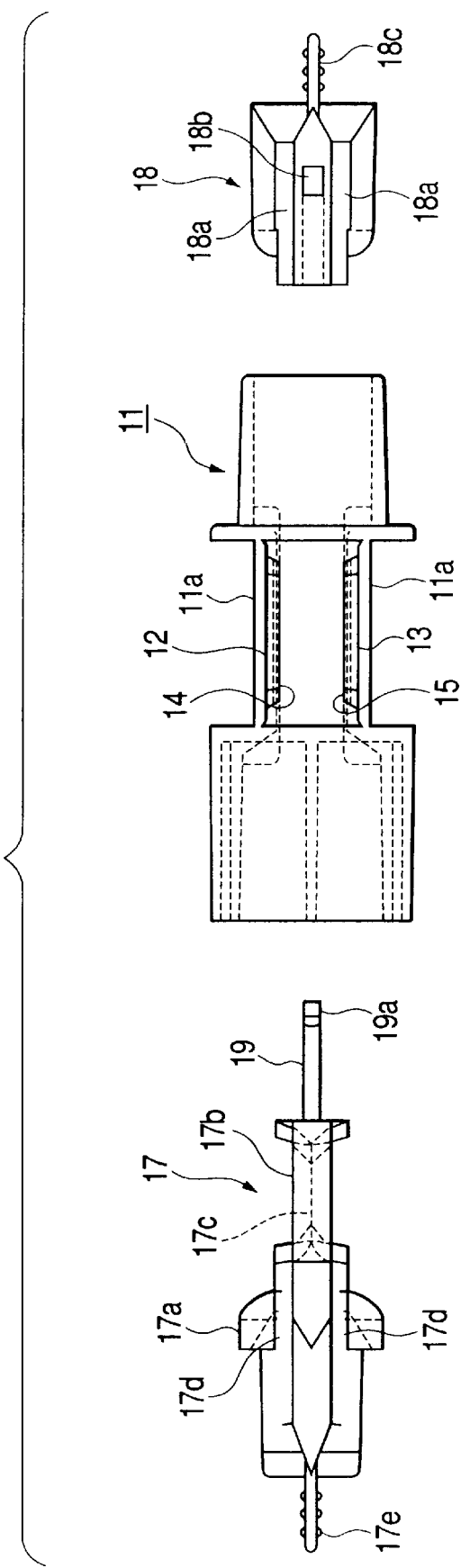
FIG. 8 is an exploded front view of FIG. 1.

Hereunder, a first embodiment of the respiratory gas sensor according to the invention will be described referring to the drawings. FIG. 1 is a longitudinally sectional view of an airway adaptor provided with an adaptor, FIG. 2 is a sectional plan view of FIG. 1, FIG. 3 is a left side view of FIG. 2, FIG. 4 is a right side view of FIG. 2, FIGS. 5, 6 and 7 are sectional views respectively taken along lines A—A, B—B, and C—C in FIG. 1, FIG. 8 is an exploded front view of FIG. 1, and FIG. 9 is an exploded plan view of FIG. 2.

The airway adaptor 11 which is a tubular member is narrowed in diameter at its central part, and formed with parallel faces 11a in parallel to an axial direction and at symmetrical positions. In respective central parts of the parallel faces 11a are airtightly provided optical windows 12, 13 which are similar to those in the conventional case. Anti-fogging films 14, 15 are formed on inner faces of the optical windows 12, 13. At least one side of the parallel faces 11a in an axial direction is integrally provided with a holding portion 16 extending radially outwardly for holding the light source and the infrared detecting portion. The light source and the infrared detecting portion are disposed outside the optical windows 12 and 13.

Figure 9:
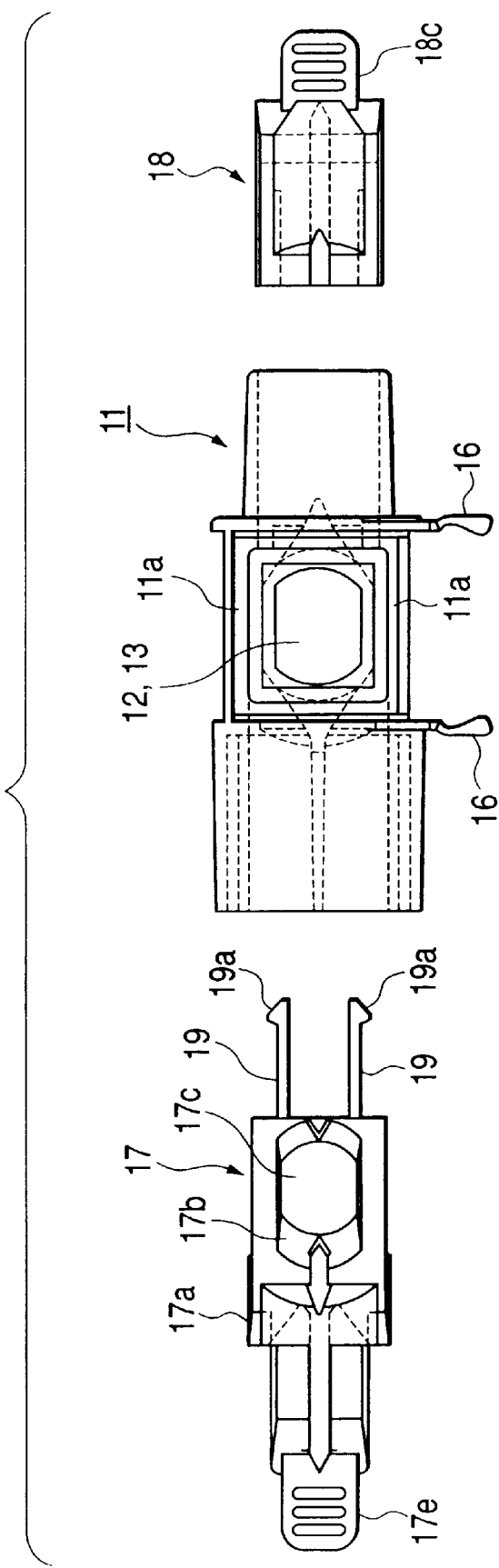
FIG. 9 is an exploded plan view of FIG. 2.

A pair of adaptors 17, 18 are engaged in the airway adaptor 11 from left and right sides, for example as shown in FIG. 9. The adaptor 17 is integrally formed in an axially center portion with a cylindrical flange portion 17a which abuts against an inner peripheral face of the airway adaptor 11 and against left sides of axially inner faces of the parallel faces 11a. On the right side of the flange portion 17a in the drawings is integrally formed a plate portion 17b along a center axis. Both faces of the plate portion 17b respectively face with the parallel faces 11a in parallel thereto leaving spaces of a determined width. Moreover, the plate portion 17b is formed with a through hole 17c on a same axis as the optical windows 12, 13. Further, the gas flows through the slits 17d formed with the flange portion 17a in parallel to the both faces of the plate portion 17b, and slits 17f formed between the both faces of the plate portion 17b and the parallel faces 11a respectively, communicating with the slits 17d. The slits 17f has a width which is larger than that of the optical windows in a direction orthogonal to the pathway.

The adaptor 18 is formed in a cylindrical shape, and its outer peripheral face abuts against inner peripheral faces on the right side of the parallel faces 11a of the airway adaptor 11. A left side end face of the adaptor 18 is in contact with right sides of the axially inner faces of the parallel faces 11a. A pair of slits 18a are formed in the adaptor 18 in parallel to an axial direction. The slits 18a communicate with the slit 17f formed between the plate portion 17b of the adaptor 17 and the parallel faces 11a of the airway adaptor 11.

Locking claws 19 are integrally provided in parallel to an axial direction at an inner end of the plate portion 17b of the adaptor 17 as shown in FIGS. 8 and 9. Angled engaging portions 19a are formed at tip ends of the locking claws 19. On the other hand, the adaptor 18 is provided with an engaging hole 18b so that the engaging portions 19a of the locking claws 19 are adapted to engage with the engaging hole 18b to be locked when the adaptors 17, 18 are fitted to each other and mounted at determined positions in the airway adaptor 11. Because each of the engaging portions 19a is formed in an angled shape having diagonal faces on both sides, they can be easily released from the engagement by pulling the adaptors 17, 18 outwardly with force while grasping grips 17e, 18c which are projectingly provided at outer end faces of the adaptors 17, 18.

According to this embodiment, the respiratory gas flows through the slit-shaped pathway formed between the entire faces of the optical windows 12, 13 and the plate portion 17b of the adaptor 17. Accordingly, the inner volume of the sensor can be reduced to decrease the dead space volume. As a result, the concentration of the respiratory gas from a neonatal and pediatric patient has a small tidal volume can be efficiently measured with high accuracy and with a simple structure. Moreover, the pathways are formed in a shape of slits between the optical windows 12, 13 and the plate portion 17b of the adaptor 17, and so, the waterdrops caused by the humidity of the respiratory gas will not remain on the inner faces of the optical windows 12, 13 forming the waterlayer. Thus, the accuracy in measurement of the gas concentration can be enhanced.

In the above described embodiment, the adaptors 17, 18 are detachable and the measuring sensor can be reused after sterilized. However, the adaptors 17, 18 may be fixed in the airway adaptor 11 so as to be disposable after used. This measuring sensor is suitable for measuring the gas concentration. However, it may be used for determining whether patients breathe or not by detecting the carbon dioxide gas.

Figure 10:
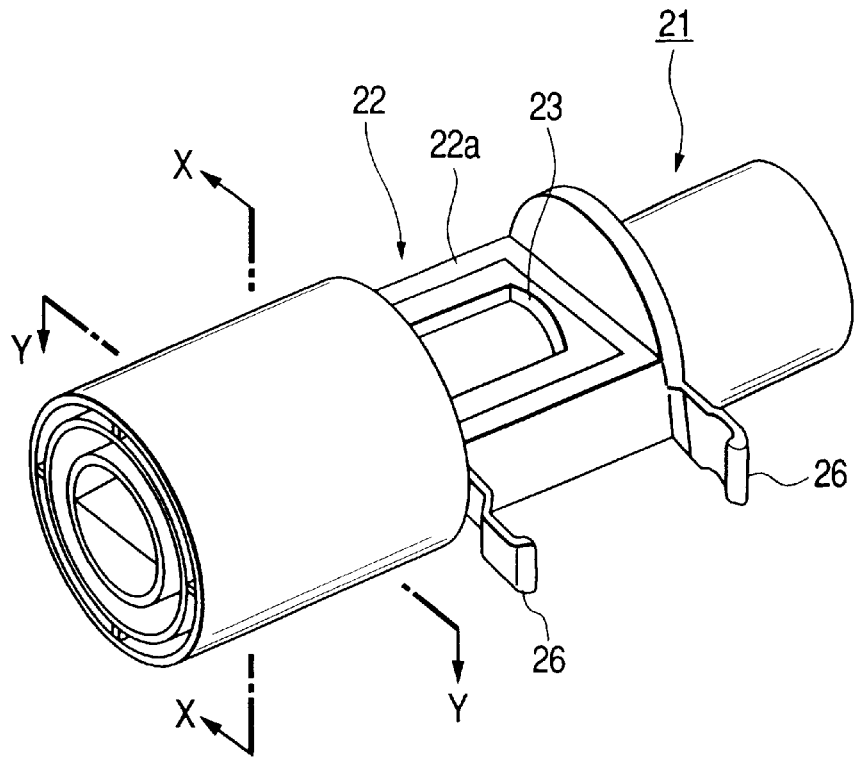
FIG. 10 is a perspective view showing an outer appearance of the airway adaptor in a second embodiment.

Then, a second embodiment according to the invention will be described. In this case, the adaptor in the first embodiment is fixed in the airway adaptor and integrally formed therewith. FIG. 10 is a perspective view showing an outer appearance of the airway adaptor, FIG. 11 is a perspective view of FIG. 10 with a portion cut away, FIG. 12 is a sectional view taken along a line X—X in FIG. 10, and FIG. 13 is a sectional view taken along a line Y—Y in FIG. 10.

As shown in FIG. 10, a central part 22 of the airway adaptor 21 which is a tubular member is formed in a box shape, and provided with a pair of parallel faces 22a. A pair of optical windows 23 are formed at the respective centers of the parallel faces 22a. Inner faces of the optical windows 23 are covered with anti-fogging films 24 thereby making the optical windows 23 airtight. At both ends of the central part 22, a pair of holding portions 26 are integrally formed projecting radially outwardly from its side parts for holding the light source and the infrared detecting portion. The light source and the infrared detecting portion are arranged at the outer periphery of a pair of the optical windows 23 (not shown).

Figure 11:
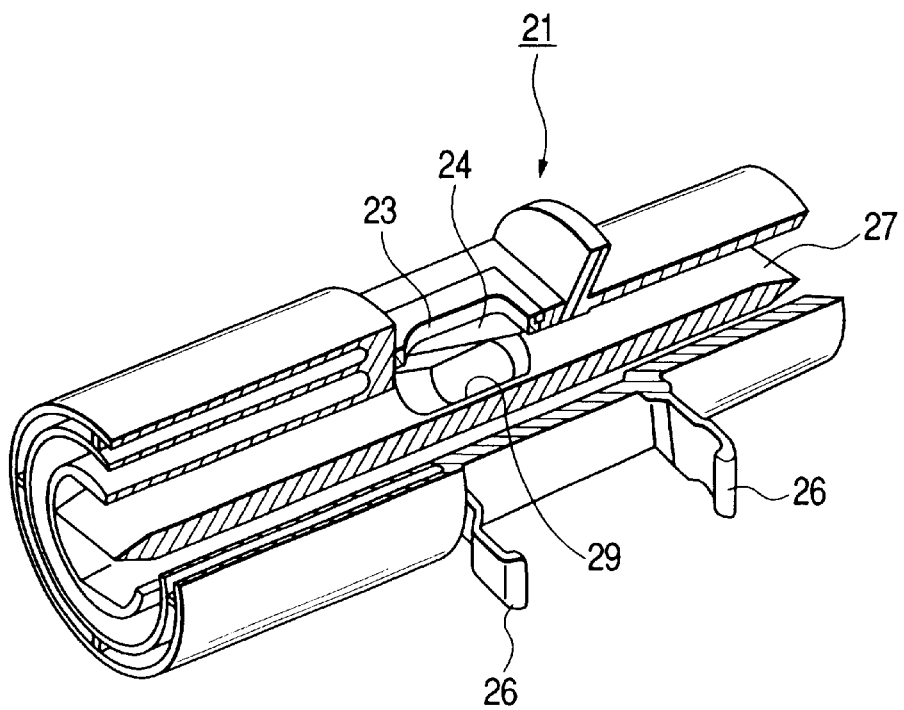
FIG. 11 is a perspective view of FIG. 10 with a portion cut away.
Figure 12:
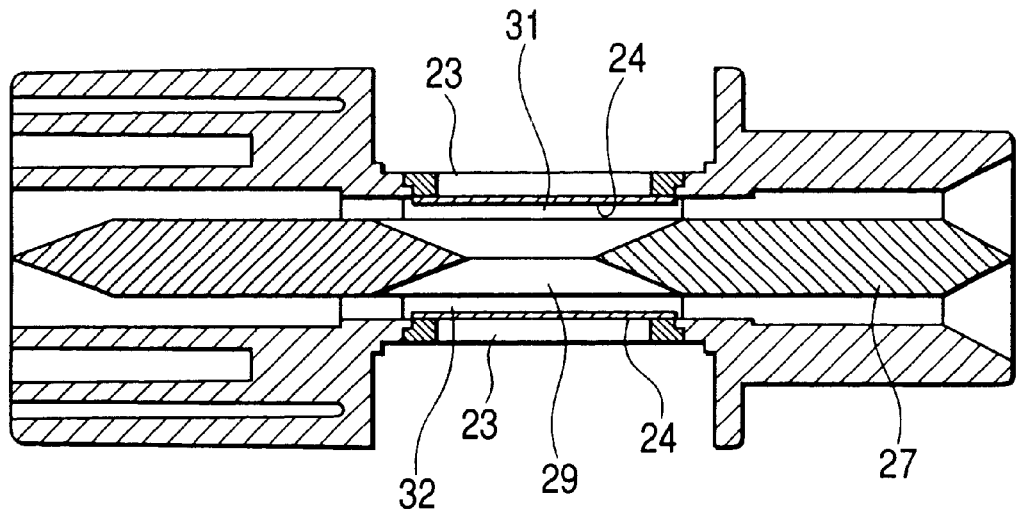
FIG. 12 is a sectional view taken along a line X—X in FIG. 10.
Figure 13:
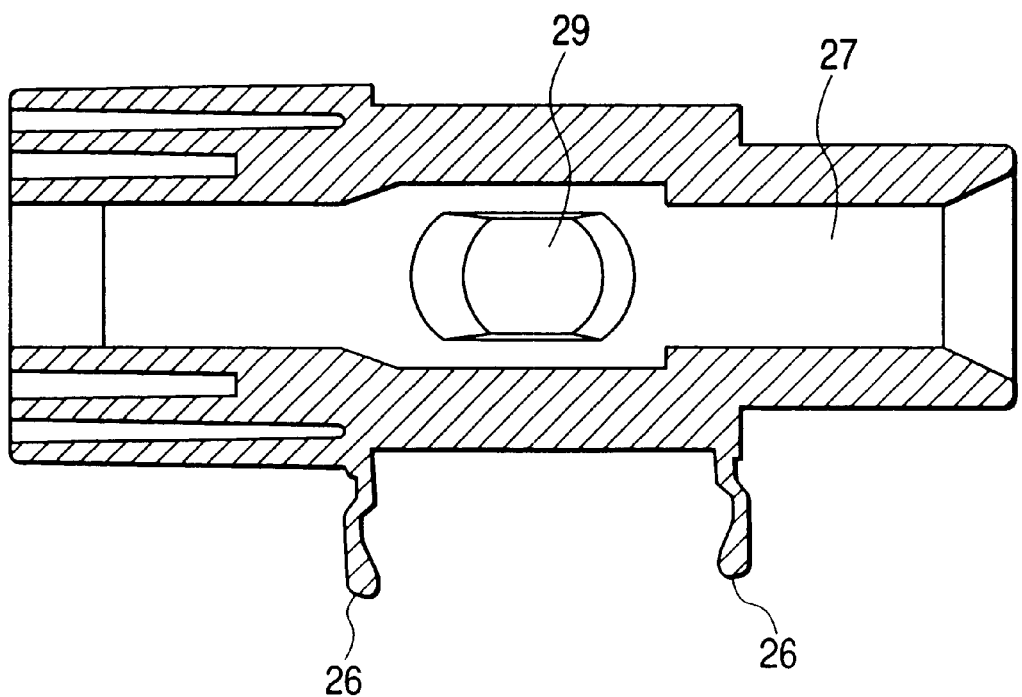
FIG. 13 is a sectional view taken along a line Y—Y in FIG. 10.
Figure 14:
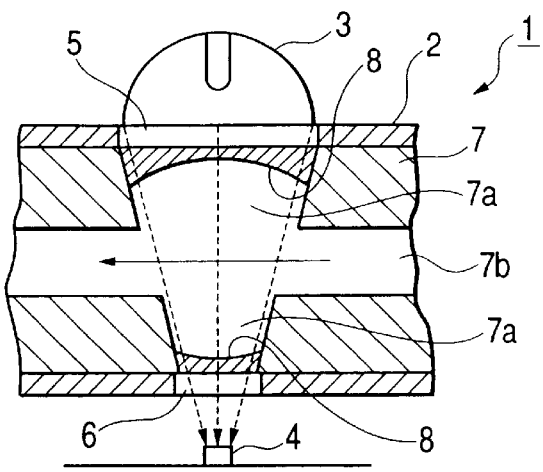
FIG. 14 is a sectional view of an essential part of prior art.

As shown in FIGS. 11 through 13, the interior of the airway adaptor 21 is divided into two pathways by a partitioning portion 27. The partitioning portion 27 is formed with a through hole 29 on a same optical axis as the optical windows 23. Slit-shaped passages 31, 32 are formed between the optical windows 23 and the partitioning portion 27. In this embodiment, a width of each of the passages 31, 32 is set to be larger than the width of the optical window 23 in a direction orthogonal to the pathway.

Figure 15:
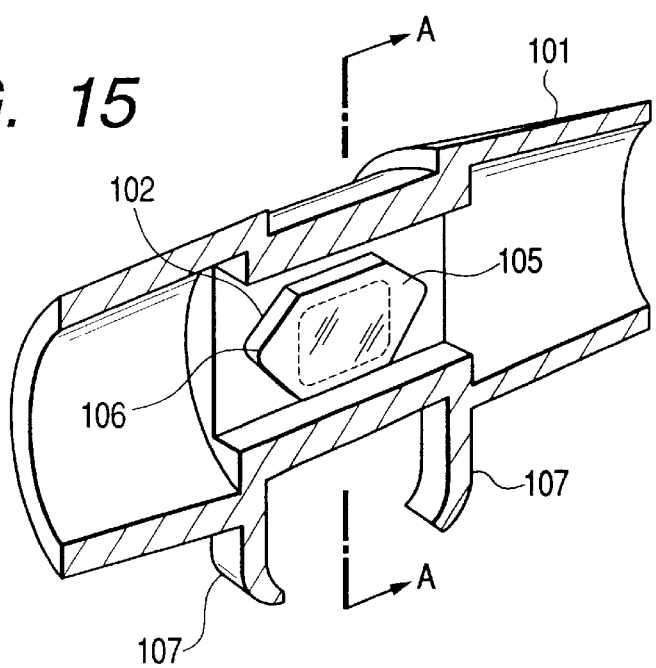
FIG. 15 is a section view showing the configuration of a modified embodiment of the airway adaptor for measurement of the gas concentration of the present invention, and taken along the axis.
Figure 16:
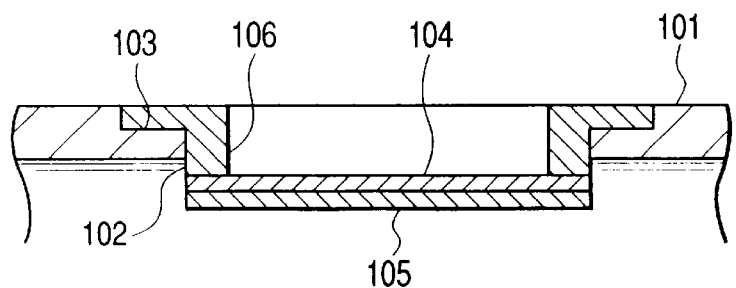
FIG. 16 is a section view taken along the line A—A.

In the first and second embodiments described above, a portion to which the optical windows 12 and 13 of the airway adaptor 11 are provided is projected inwardly to prevent waterlayer or waterdrops from being adhered on or passed over the optical windows 12 and 13. The modified embodiments are shown in FIGS. 15 to 18. Referring to FIGS. 15 and 16, frame 106 serving as the frames are formed into a hexagonal shape. The frame are fitted into the apertures 102 which are formed at opposed positions of the side walls of the tubular member 101, respectively, while a flange of each of the frame abuts against the step portion 103 of the corresponding aperture 102, so as to be airtightly fixed to the aperture. The portion of the inner side of each of the frame 106 is inwardly protruded from the inner peripheral face of the tubular member 101. The transparent sheet 104 on the inner surface of which an anti-fogging layer 105 is formed is fixed to an end surface of the frame 106 which is inwardly protruded into the tubular member 101. The reference numeral 107 denotes an attachment portion for fixing an unit having an infrared light emitting unit and a light receiving unit which are not shown, to the tubular member 101.

Figure 17:
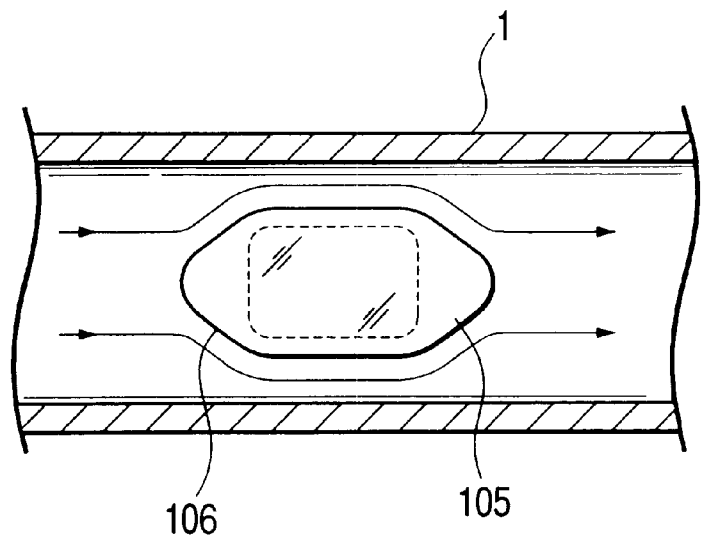
FIG. 17 is a view showing a flow of waterdrops in a flow tube of FIG. 15.
Figure 19:
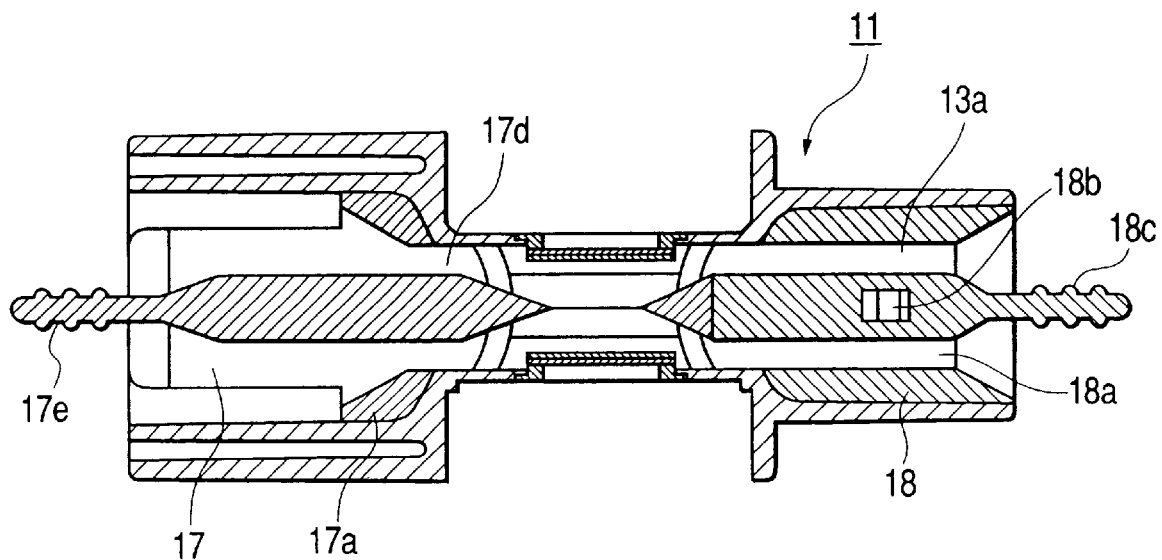
FIG. 19 shows a longitudinal sectional view in the state that the adaptor described in the first embodiment is attached.
Figure 20:
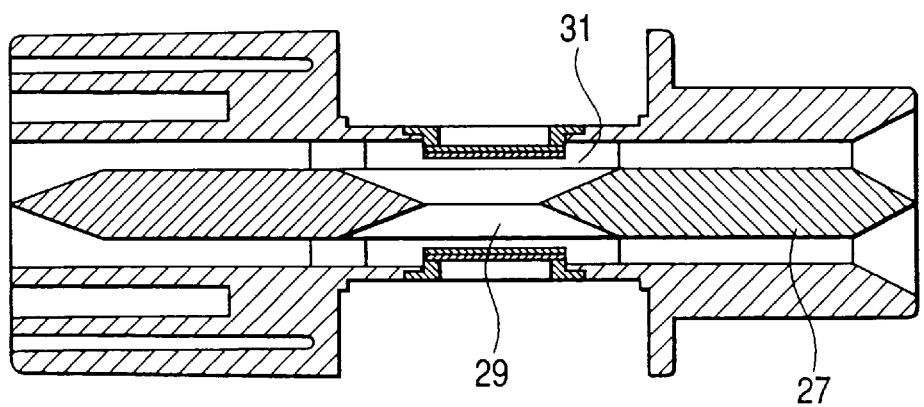
FIG. 20 shows a longitudinal sectional view in the state that the adaptor described in the first embodiment is fixed in the airway adaptor through uniformly forming each other.

According to the embodiment, when the airway adaptor is attached to a flow path of a, respirator, waterdrops or waterlayer due to the humidity of respiratory gas flowing through the tubular member 101 flows along the inner wall of the tubular member 101. At this time, as shown in FIG. 17, the waterdrops or waterlayer pass over the outer side of each of the frame 106, space between the larger part in width of the slits and the inner circumference wall of the tubular member, as the water path, which are protruded from the inner face of the tubular member 101. Therefore, the waterdrops or waterlayer are prevented from passing over the anti-fogging layers 105 of the transparent sheets 104 which stretch on the inner faces of the frame 106. As a result, infrared light passing through the transparent sheets 104 is not interrupted by the waterdrops or waterlayer, and hence an error does not occur in measurement of the concentration of carbon dioxide gas in respiratory gas. FIG. 19 shows a longitudinal sectional view in the state that the adaptor described in the first embodiment is attached. FIG. 20 shows a longitudinal sectional view in the state that the adaptor described in the first embodiment is fixed in the airway adaptor through uniformly forming each other. In both of them, a portion to which the optical windows 12 and 13 of the airway adaptor 11 are provided is projected inwardly to form the slit or passage so as to prevent waterdrops or waterlayer from being adhered on or passed over the optical windows 12 and 13.

Figure 18:
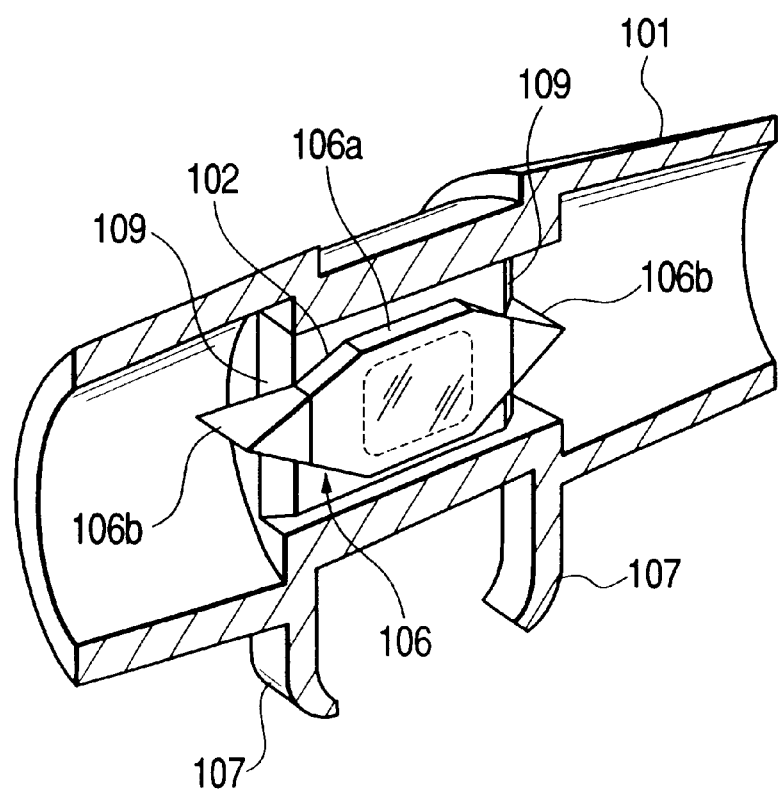
FIG. 18 is a section view showing the configuration of another modified embodiment of the airway adaptor of the present invention.

FIG. 18 shows another example of the modified embodiment regarding a portion to which the optical windows 12 and 13 of the airway adaptor 11 are provided projected inwardly. In stead of using the airway adaptor shown in the first and second embodiments, it is capable for employing the airway adaptor as shown in FIG. 18. A detailed description will be described hereinbelow.

As shown in FIG. 18, it is applicable for forming the frame 106 to an area positioned beyond a narrowed portion of the tubular member 101. In this circumstance, the frame 106 is constituted of the body portion 106a and a pair of end portions 106b, and is formed into a hexagonal shape. The body portion is slightly different from the embodiment described above. However, the substantive structure is the same as the embodiment described above. Namely, the body portion 106a is sealingly fitted on the aperture portion in such a manner that the flange portion of the body portion abuts against the flange portion of the stepped portion 103 of the aperture 102 (as shown in FIG. 16).

Each end portion 106b is uniformly formed with the tubular member at the inner portion thereof. The frame 106 extends from the inlet to the outlet through the narrowed portion. As a result, since the slit as waterpath is divided by the frame 106 before waterdrops enter into the window 102, the device is more free from the phenomenon that the waterdrops or waterlayer pass over the transparent sheets.

As shown in FIG. 18, the taper portion is formed at an inner apex portion of the tubular member on a narrowed portion 20, that is, the enter portion is defined at the entrance portion of the narrowed portion 20. As a result, it is avoided to splash the waterdrop or waterlayers by hitting against an entrance portion of the narrowed portion 20 and to more effectively prevent the waterdrops or waterlayer from being passed over the transparent film.

In the embodiment described above, the frame 106 is formed into a hexagonal shape. The shape of the frame 106 is not restricted to a hexagon. The frame may have any other shape as far as the shape produces a small flow resistance against respiratory gas flowing through the tubular member 101. Sapphire may be applied as optical windows, as long as a frame is formed.

As described above, according to the embodiment, the airway adaptor have a slit or passage as water path for preventing the waterdrops or waterlayer from being passed over the transparent film. Therefore, waterdrops or waterlayer due to the humidity of respiratory gas flowing through the tubular member pass over the outer side of each of the frames which are protruded from the inner face of the tubular member, so that the waterdrops or waterlayer are prevented from passing over the transparent films which stretch on the inner faces of the frames. As a result, infrared light passing through the transparent films is not interrupted by the waterdrops or waterlayer. Consequently, an error does not occur in measurement of the concentration of carbon dioxide gas, thereby allowing measurement to be stably performed for a long term.

According to this embodiment, the respiratory gas flows through the slit-shaped passages 31, 32 formed between the entire faces of the optical windows 23 and the partitioning portion 27.

Accordingly, in the same manner as in the first embodiment, the inner volume of the sensor can be reduced to decrease the dead space volume that results in improvement of response and measurement-accuracy. Moreover, waterdrops caused by the humidity of the respiratory gas or waterlayer will not pass over or remain on the inner faces of the optical windows 23. Further according to this embodiment, because there is no need of an adaptor, the gas sensor can be easily manufactured and simply operated in use. Further, this sensor can be disposable after the use, because it can be manufactured at a low cost.

As described above, according to the respiratory gas sensor in the invention, the slit-shaped pathways are formed in the sensor on its outer periphery at positions respectively facing with and adjacent to the optical windows, and each of the slits has a width larger than that of each of the optical windows in a direction orthogonal to the pathway. Therefore, the inner volume of the sensor can be reduced to decrease the dead space volume. As a result, the sensor can efficiently measure the gas concentration in the respiratory gas from a neonatal and pediatric patient who has a small tidal volume, with a simple structure and with high accuracy without being affected by the waterdrops or waterlayer. Further, because the respiratory gas passes along the entire surfaces of the optical windows, the waterdrops caused by the humidity of the respiratory gas will not pass over or remain inside the optical windows forming the waterlayer, and the accuracy in measuring the gas concentration can be enhanced.

What is claimed is:

1. A respiratory gas sensor comprising:
   a tubular member including a pathway formed therein;
   a pair of optical windows formed airtightly in a circumferential wall of the tubular member for allowing light to pass through said optical windows from the exterior into gas flowing through the pathway;
   an adaptor fitted to an inner peripheral face of the tubular member and provided with a through hole at a position in alignment with the optical windows such that the through hole is positioned in a space between the pair of optical windows, and
   slits formed in the adaptor in an axis direction in such a manner that the slits face and are positioned adjacent to the optical windows formed on a periphery of the tubular member, respectively.

2. The respiratory gas sensor as claimed in claim 1, wherein said each slit has a width larger than that of the optical window in a direction orthogonal to the axis direction of said pathway.

3. The respiratory gas sensor as claimed in claim 2, further comprising: a water path formed between said larger part in width of said slit and the inner circumference wall of said tubular member to prevent waterdrops or waterlayer from being passed over said optical windows.

4. A respiratory gas sensor as claimed in claim 1, the adaptor is divided in axially opposite sides of the optical windows.

5. A respiratory gas sensor as claimed in claim 4, wherein adaptor to be divided is fixed inside the tubular member.

6. A respiratory gas sensor as claimed in claim 1, wherein the adaptor to be divided is detachably connected with each other inside the tubular member.

7. A respiratory gas sensor as claimed in claim 1, further comprising:
   anti-fogging films provided on inner faces of the optical windows.

8. A respiratory gas sensor comprising:
   a tubular member including a pathway formed therein;
   a pair of optical windows formed airtightly in a peripheral wall of the tubular member for allowing light to pass through said optical windows from the exterior into the gas flowing through the pathway;
   a partitioning portion for dividing the pathway into plurality of passages, the partitioning portion including:
     a through hole for allowing light to pass from one of the optical windows to the other, the passages divided by the partitioning portion being adapted to extend along the optical windows respectively.

9. The respiratory gas sensor as claimed in claim 8, wherein said partitioning portion has a width larger than that of the optical windows in a direction orthogonal to the pathway.

10. A respiratory gas sensor as claimed in claim 8, further comprising:
    anti-fogging films provided on inner faces of the optical windows.

11. The airway adaptor as claimed in claim 8, further comprising:
    a frame protruded from on an inner circumference wall of said tubular member.

12. The airway adaptor as claimed in claim 11, wherein said optical windows are positioned at inner surface of said protruded frame, respectively.

13. The airway adaptor as claimed in claim 11, wherein said frame is formed to an area positioned beyond a narrowed portion of said tubular member.

14. The airway adaptor as claimed in claim 8, wherein said tubular member has a taper portion formed on a narrowed portion thereof.

15. A respiratory gas sensor comprising:
    a tubular member including a pathway formed therein;
    a pair of optical windows formed airtightly in a circumferential wall of said tubular member for allowing light to pass through said optical windows from the exterior into gas flowing through the pathway;
    an adaptor fitted to an inner peripheral face of said tubular member, wherein there are slits between said adaptor and inner planar surfaces, having said windows, of said tubular member, respectively.

16. The respiratory gas sensor according to claim 15, wherein said adaptor is provided with a through hole at a position in alignment with said pair of optical windows such that the through hole is positioned in a space between said pair of optical windows.

17. The respiratory gas sensor according to claim 15, further comprising:
    a frame protruded from on an inner circumference wall of said tubular member.

18. The respiratory gas sensor according to claim 15, further comprising:
    two frames protruded from on an inner circumference wall of said tubular member,
    wherein said optical windows are positioned at an inner surface of said protruded frames, respectively.

19. The respiratory gas sensor according to claim 15, further comprising:
    two frames protruded from on an inner circumference wall of said tubular member,
    wherein said frames are formed to an area positioned beyond a narrowed portion of said tubular member.

20. The respiratory gas sensor according to claim 15, wherein each of said slits has a width larger than that of said optical windows in a direction orthogonal to the axis direction of the pathway.

21. A respiratory gas sensor comprising:
    a tubular member including a pathway formed therein;
    a pair of optical windows formed airtightly in a circumferential wall of said tubular member for allowing light to pass through said optical windows from the exterior into gas flowing through the pathway;
    an adaptor fitted to an inner peripheral face of said tubular member; and
    slits formed in said adaptor in an axis direction in such a manner that the slits face, and do not allow the adaptor to be attached to, an inner planar surface of said tubular member, the inner planar surface having said windows.

22. The respiratory gas sensor according to claim 21, wherein said adaptor is provided with a through hole at a position in alignment with said pair of optical windows such that the through hole is positioned in a space between said pair of optical windows.

23. The respiratory gas sensor according to claim 21, further comprising:
    a frame protruded from on an inner circumference wall of said tubular member.

24. The respiratory gas sensor according to claim 21, further comprising:
    two frames protruded from on an inner circumference wall of said tubular member,
    wherein said optical windows are positioned at an inner surface of said protruded frames, respectively.

25. The respiratory gas sensor according to claim 21, further comprising:
    two frames protruded from on an inner circumference wall of said tubular member,
    wherein said frames are formed to an area positioned beyond a narrowed portion of said tubular member.

26. The respiratory gas sensor according to claim 21, wherein each of said slits has a width larger than that of said optical windows in a direction orthogonal to the axis direction of the pathway.

27. A respiratory gas sensor comprising:
    a tubular member including a pathway formed therein;
    a pair of optical windows formed airtightly in a circumferential wall of said tubular member for allowing light to pass through said optical windows from the exterior into gas flowing through the pathway;
    a partitioning portion for dividing the pathway into a plurality of passages, wherein the passages are positioned between said partitioning portion and inner planar surfaces, having said windows, of said tubular member, respectively.

28. The respiratory gas sensor according to claim 27, wherein said partitioning portion is provided with a through hole at a position in alignment with said pair of optical windows such that the through hole is positioned in a space between said pair of optical windows.

29. The respiratory gas sensor according to claim 27, further comprising:
    a frame protruded from on an inner circumference wall of said tubular member.

30. The respiratory gas sensor according to claim 27, further comprising:
    two frames protruded from on an inner circumference wall of said tubular member,
    wherein said optical windows are positioned at an inner surface of said protruded frames, respectively.

31. The respiratory gas sensor according to claim 27, further comprising:
    two frames protruded from on an inner circumference wall of said tubular member,
    wherein said frames are formed to an area positioned beyond a narrowed portion of said tubular member.

32. The respiratory gas sensor according to claim 27, wherein each of said passages has a width larger than that of said optical windows in a direction orthogonal to the axis direction of the pathway.

33. A respiratory gas sensor comprising:
    a tubular member including a pathway formed therein;
    a pair of optical windows formed airtightly in a circumferential wall of said tubular member for allowing light to pass through said optical windows from the exterior into gas flowing through the pathway;
    a partitioning portion for dividing the pathway into a plurality of passages, wherein said partitioning portion is not attached to an inner planar surface of said tubular member, the inner planar surface having said windows.

34. The respiratory gas sensor according to claim 33, wherein said partitioning portion is provided with a through hole at a position in alignment with said pair of optical windows such that the through hole is positioned in a space between said pair of optical windows.

35. The respiratory gas sensor according to claim 33, further comprising:
a frame protruded from on an inner circumference wall of said tubular member.

36. The respiratory gas sensor according to claim 33, further comprising:
two frames protruded from on an inner circumference wall of said tubular member,
wherein said optical windows are positioned at an inner surface of said protruded frames, respectively.

37. The respiratory gas sensor according to claim 33, further comprising:
two frames protruded from on an inner circumference wall of said tubular member,
wherein said frames are formed to an area positioned beyond a narrowed portion of said tubular member.

38. The respiratory gas sensor according to claim 33, wherein each of said passages has a width larger than that of said optical windows in a direction orthogonal to the axis direction of the pathway.

39. The respiratory gas sensor according to claim 15, further comprising anti-fogging films provided on inner faces of said optical windows.

40. The respiratory gas sensor according to claim 21, comprising anti-fogging films provided on inner faces of said optical windows.

41. The respiratory gas sensor according to claim 27, comprising anti-fogging films provided on inner faces of said optical windows.

42. The respiratory gas sensor according to claim 33, comprising anti-fogging films provided on inner faces of said optical windows.

* * * * *